United States Patent
Rousseaux et al.

(12)

(10) Patent No.: US 6,827,927 B1
(45) Date of Patent: Dec. 7, 2004

(54) GADOLINIUM COMPLEX TETRAMIDES AND USE IN MEDICAL IMAGING

(75) Inventors: Olivier Rousseaux, Senlis (FR); Christian Simonot, Paris (FR)

(73) Assignee: Guerbet, Villepinte (FR)

( * ) Notice: Subject to any disclaimer, the term of this patent is extended or adjusted under 35 U.S.C. 154(b) by 0 days.

(21) Appl. No.: 09/926,589

(22) PCT Filed: May 19, 2000

(86) PCT No.: PCT/FR00/01382

§ 371 (c)(1),
(2), (4) Date: Nov. 21, 2001

(87) PCT Pub. No.: WO00/71526

PCT Pub. Date: Nov. 30, 2000

(30) Foreign Application Priority Data

May 21, 1999 (FR) .............................. 99 06517

(51) Int. Cl.$^7$ ....................... A61B 5/055; C07D 255/02; C07D 257/02

(52) U.S. Cl. ..................................... 424/9.363; 540/474
(58) Field of Search ............................ 424/9.363, 9.361, 424/936, 1.65; 534/15, 16; 540/465, 474

(56) References Cited

U.S. PATENT DOCUMENTS 5,886,158 A * 3/1999 Meyer et al. .................. 534/16
6,177,562 B1 * 1/2001 Uggeri et al. ................ 540/474
6,187,285 B1 * 2/2001 Meyer et al. ............... 424/1.65

FOREIGN PATENT DOCUMENTS

WO    WO 97/01359    *  1/1997

* cited by examiner

*Primary Examiner*—Michael G. Hartley
(74) *Attorney, Agent, or Firm*—Jacobson Holman PLLC

(57) ABSTRACT

The invention concerns a racemic compound of the pair of enantiomers of formula (III) wherein R represents an alkyl group or a phenyl group optionally substituted.

2 Claims, No Drawings

GADOLINIUM COMPLEX TETRAMIDES AND USE IN MEDICAL IMAGING

This is a 371 of PCT/FR00/01382 filed May 19, 2000, the disclosure of which is incorporated herein by reference.

The present invention relates to tetramides which are derived from the pair of RRRR/SSSS enantiomers of tetra (α-carboxyethyl)gadoterate, represented by the formulae

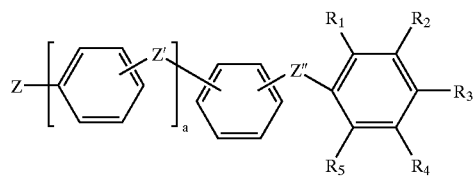

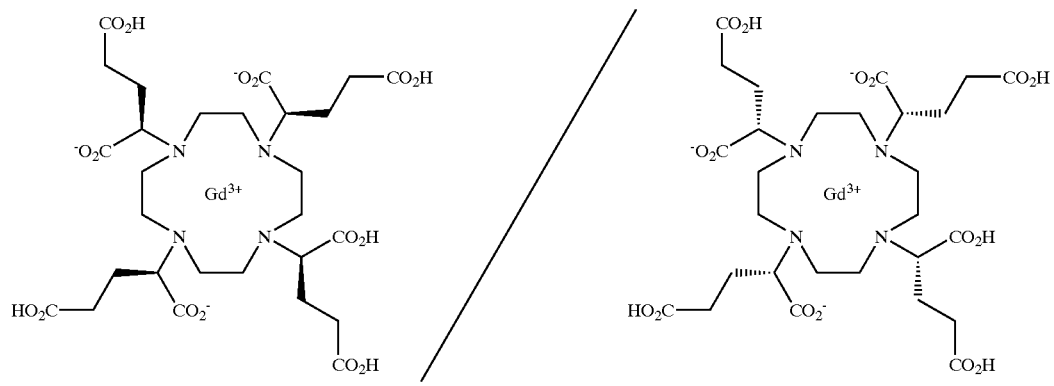

It is disclosed in EP 0 661 279 that the amides of formula II

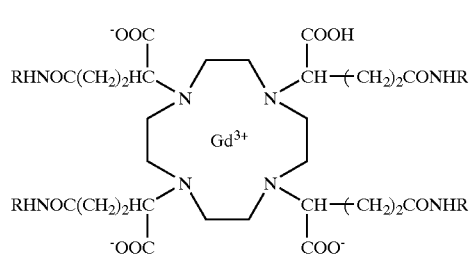

in which R is a bulky hydrophilic group with a molecular mass or greater than 200, exhibit a longitudinal relativity $r_1$ which is markedly superior to those of the chelates not carrying the bulky side group $(CH_2)_2CONHR$ and can be used as contrast agents in magnetic resonance diagnostic imaging.

WO 97/01359 relates to the products of formula II in which R is a group of formula

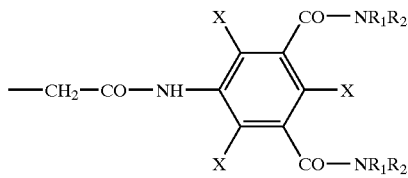

Application EP 98 403108 of Dec. 9, 1998 relates to the products of formula II in which R is the following group It is known that the relaxivity $r_1$ of a gadolinium chelate is a complex function of various more or less independent factors, including the electronic correlation time, rotation correlation time and water exchange time, which factors depend in particular on the spatial structure of the chelating agent around the paramagnetic cation, so that 2 stereoisomers can have substantially different relaxivities.

Furthermore, it is essential for the specific characteristics of a pharmaceutical product to be reproducible in terms of effectiveness and of toxicity between successive manufacturing batches and it can be difficult to ensure such reproducibility in the presence of numerous stereoisomers because of their substantial differences in chemical reactivity and in physical properties.

It was thus desirable to find a process which makes it possible, at the industrial stage under acceptable economic conditions, to obtain a mixture of stereoisomers of the amides of formula II in exactly defined proportions and thus to isolate, with good yields, one of the possible racemic compounds which does not comprise the other stereoisomers and which exhibits an advantageous relaxivity $r_1$ in the range of the fields currently used clinically, namely between 0.5 and 1.5 tesla.

The racemic compounds according to the invention are represented by the formula III

III

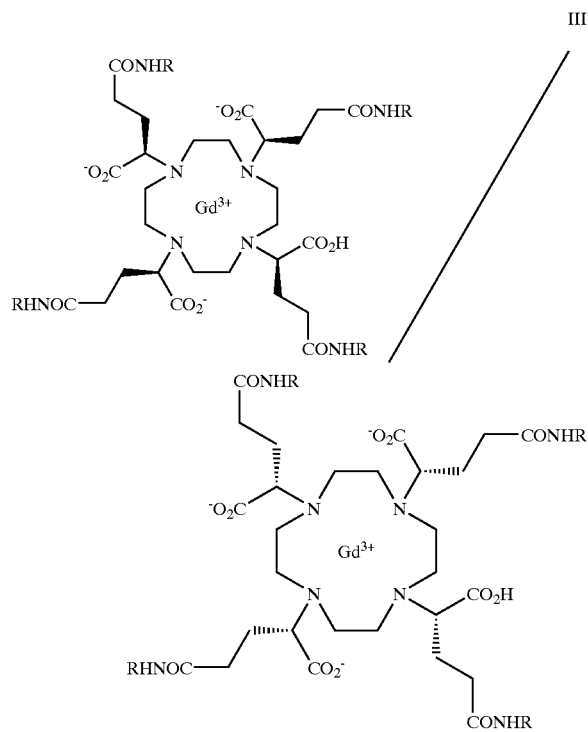

in which R is a phenyl group or ($C_1$–$C_8$) alkyl group which are substituted or interrupted by one or more groups selected from phenyl, alkyl, oxy, amino or amido groups, which may or may not be substituted by alkyl, it being possible for the phenyl groups to be substituted by OH, Br, Cl, I, ($C_1$–$C_8$) alkyl, ($C_1$–$C_8$)alkyleneoxy, $NO_2$; $NR_xR_y$, $NR_xCOR_y$, CON-$R_xR_y$ or $COOR_x$, $R_x$ and $R_y$ being ($C_1$–$C_8$)alkyl or H, and it being possible for the linear or branched or cyclic alkyl groups to be hydroxylated, and the salts of these acids with inorganic or organic bases, such as NaOH, KOH, N-methylglucamine, tris-(hydroxymethyl)aminomethane, lysine or diethanolamine.

Preference is given, among these, to the compounds in which

R is a group of formula

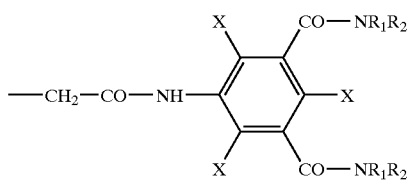

in which X is Br or I, $R_1$ is H, ($C_1$–$C_3$)alkyl or ($C_2$–$C_8$)mono- or polyhydroxyalkyl and $R_2$ is ($C_2$–$C_8$) mono- or polyhydroxyalkyl, or else $R_1$ is H and $R_2$ is a group of formula

A

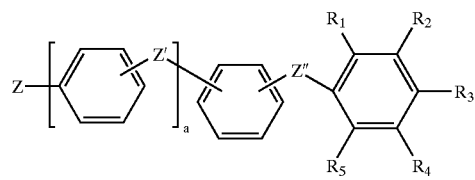

X being as defined above and $R'_1$ and $R'_2$ taking any one of the meanings given for $R_1$ and $R_2$, with the exception of A, it being understood that —CO—$NR_1R_2$ or —CO—$NR'_1R'_2$ comprise at least two hydroxyl groups, and those in which R is a group

in which a is 1 or 2,
Z is a bond, $CH_2$, $CH_2CONH$ or $(CH_2)_2NHCO$,
Z' is a bond, O, S, NQ, $CH_2$, CO, CO—NQ, NQ—CO, NQ—CO—NQ or CO—NQ—$CH_2$—CONQ,
Z" is CO—NQ, NQ—CO, CO—NQ—$CH_2$—CO—NQ or NQ—CO—$CH_2$—NQ—CQ, with Q being H or an optionally hydroxylated ($C_1$–C4) alkyl group,
$R_1$, $R_2$, $R_3$, $R_4$ and $R_5$, independently of one another, are selected from H, Br, Cl, I, CO—$NQ_1Q_2$ or $N(Q_1)$—CO—$Q_2$, and $Q_1$ and $Q_2$, which are identical or different, are selected from optionally hydroxylated ($C_2$–$C_6$) alkyl groups optionally interrupted by an oxygen atom, so that $Q_1$ and $Q_2$ together comprise from 4 to 10 OH groups, it being understood that at least 1 and at most 2 $R_1$, $R_2$, $R_3$, $R_4$ and $R_5$ groups are amide groups.

The racemic compounds of the invention can be prepared by a method known per se by reaction of the amine $RNH_2$ with the pair of complexes of the enantiomeric octaacids of formula I in aqueous solution with an agent which activates carboxyl functional groups under conventional conditions for peptide condensations, as disclosed in the abovementioned patents, for mixtures of isomers.

Some of the isomers of 1,4,7,10-tetraazacyclododecane-1,4,7,10-tetra(2-glutaric acid), obtained by hydrolysis of the corresponding ethyl esters, separated by silica liquid chromatography and crystallization from water, have been described by Judith A. K. Howard et al. in Chem. Commun., 1381–1382 (1998).

A process which can be operated industrially has now been found which makes it possible to obtain the pair of RRRR/SSSS enantiomers starting from the mixture of the stereoisomers of the gadolinium complex of this octaacid resulting from the substitution, by a conventional method, of the nitrogen atoms of 1,4,7,10-tetraazacycladodecane. It consists in carrying out the isoomerization by simple heating in aqueous solution at acidic pH, preferably between 2 and 4.5 and better still between 2.5 and 3.5, and at a temperature of greater than 70° C., preferably of greater than 90° C. and better still at reflux of the solution, for the time needed to obtain the racemic compound of the invention, i.e. from a few hours to a few days, in particular 35 to 45 hours at reflux at approximately pH 3.

The starting mixture of the stereoisomers can be obtained by the action of the compound of formula R'OOC—CHX—(CH$_2$)$_2$—COOR', in which R'=H or (C$_1$–C$_3$)alkyl and X is a leaving group in a nucleophilic substitution, in particular a halogen atom, preferably bromine, or a sulphonate or tosylate or triflate group, which reaction is followed by the hydrolysis of the ester functional groups, in particular by the action of an alkaline carbonate or hydroxide in an alcoholic, agueous/alcoholic or aqueous medium.

A person skilled in the art will select, during preliminary trials, the concentration of the solution, the pH, the temperature and the duration of the heating in order to carry out complete isomerization without significant decomposition, in particular according to the product and the amount treated.

It is surprising that, under these conditions, the chelate is not decomplexed and that the decomposition of the ligand is negligible and that, in addition, the pair of enantiomers which is finally isolated comprise less than 15% of the 3 pairs formed on conclusion of a conventional synthesis, which consists in hydrolysing, in basic medium, the product obtained by reaction of ethyl 2-bromoglutarate with the heterocycle and in then carrying out its complexation by the action of GdCl$_3$ or to Gd$_2$O$_3$.

Thus, according to another of its aspects, the present invention relates to a process comprising the stages consisting:

1—in keeping an aqueous solution of the mixture of the stereoisomers of the gadolinium complex of 1,4,7,10-tetraazacyclododecane-1,4,7,10-tetra(2-glutaric acid), with a pH of between 2 and 4.5, at a temperature of greater than 70° C. for a few hours to a few days, so as to obtain the racemic mixture of octaacids of formula:

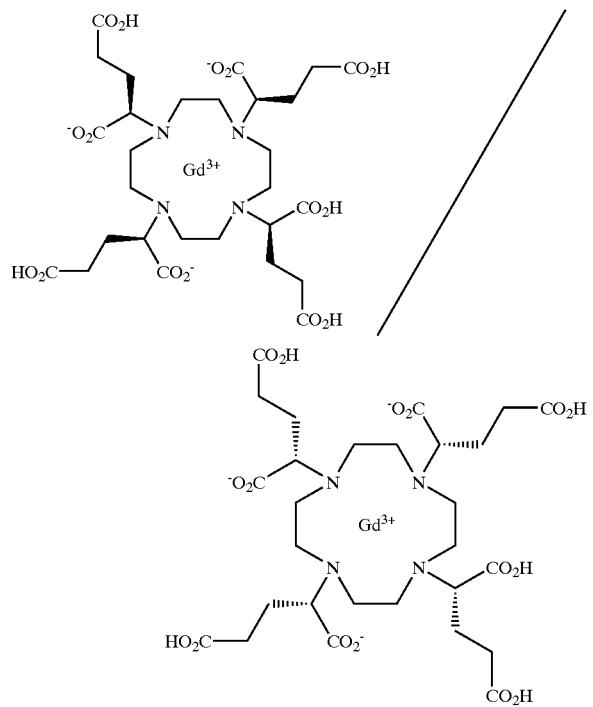

2—in reacting this mixture with the amine RNH$_2$, R being defined above for the Formula III, with an agent which activates the acid functional group.

The starting mixture of the stereoisomers of the gadolinium complex of 1,4,7,10-tetraazacyclododecane-4,7,10-tetra(2-glutaric acid) of formula;

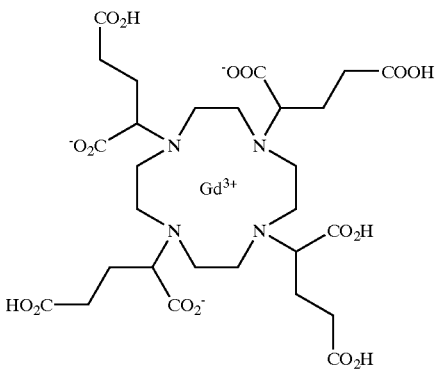

can be obtained in a simple fashion by employing a process comprising the stages consisting in:

reacting 1,4,7,10-tetraazacyclododecane with a compound of formula R'OOC—CHX(CH$_2$)$_2$—COOR' in which R' is a hydrogen atom or (C$_1$–C$_3$)alkyl and X is a leaving is group;

conventionally hydrolysing the ester functional group of the resulting compound when R' is other than H; and complexing the compound thus obtained with the gadolinium ion.

Mention may be made, as leaving group which can be used, of the sulphonate, tosylate and triflate groups.

The invention also relates to compositions for nuclear magnetic resonance medical imaging which comprise the racemic compounds of the invention in combination with conventional vehicles and additives. The doses at which these contrast agents will be administered depend on their magnetic efficiency, on their biodistribution and on their administration route, as on the size of the subject, on the organ to be observed and on the nature of the pathology. For an intravascular administration, the unit concentration will be between 0.5 and 5 mM for an adult, presented in aqueous solution.

In that which follows, examples of the preparation of the compounds of the invention are described.

The isolated products are characterized by their retention times (t$_r$) in high performance liquid chromatography (HPLC). Their molecular masses were determined by mass spectrometry (electrospray).

EXAMPLE 1

Compound of Formula II in which

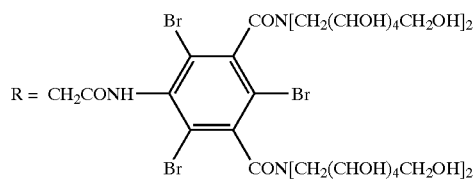

A. Gadolinium chelate of 1,4,7,10-tetraazacyclo-dodecane-1,4,7,10-tetra(2-glutaric acid) (mixture of the 6 diastereoisomers).

1.—30 g of sodium carbonate and then 78 g of ethyl 2-bromoglutarate, prepared, for example, as described in Acta Chim. Acad. Sci. Hung., 41(3), 331–6 (1964), are introduced into a solution of 25 g of 1,4,7,10-tetraazacyclododecane in 280 ml of acetonitrile. The medium is brought to its reflux temperature for one day, during which 78 g of the brominated derivative with 30 g of sodium carbonate are added on two occasions. After cooling, the precipitate is filtered off and the organic phase is washed with water before being extracted with a dilute aqueous hydrochloric acid solution. The aqueous phase, brought to approximately pH 3–4, is subsequently extracted with toluene.

The desired product is purified by silica chromatography, elution being carried out with methylene chloride, optionally as a mixture with acetone.

2.—Hydrolysis of the ester functional groups:

46 g of the octaester are introduced into a solution of 52 ml of ethanol and 350 ml of water, to which 50 g of NaOH pearls have been added.

After stirring for two days at 80° C., 500 ml of cation exchange resin in the weak acid form are introduced into the cooled solution for neutralization and then, after separation of the solid phase, 500 ml of anionic exchange resin in the strong base form are introduced. The resin is separated and introduced into 500 ml of 6N aqeous acetic acid solution; the final product, which has passed into solution, is isolated in the form of a powder by evaporating the solvent under vacuum.

HPLC: 25 cm×4.6 mm column of Nucleosil® C18–100–5 μm silica gel.

Eluent: aqueous $H_2SO_4$ (0.1%) for 10 minutes and then with 0 to 10% (v/v) of $CH_3CN$ over 10 minutes:

flow rate=1 ml/min; T=25° C.;

$t_r$=5.4, 8.7, 10.2 and 14 minutes (isomers)

($CH_3COOH$–$t_r$=4.5 minutes)

3.—Complexation:

With gadolinium oxide: 0.47 g of gadolinium oxide is introduced into 30 ml of a solution, at a pH of 5.5 to 6, of 2 g of the preceding octaacid and the mixture is maintained at 80° C. for 3 hours, during which the pH is adjusted, if necessary. The medium is filtered, concentrated to a third and then poured into 100 ml of ethanol. The precipitate formed can be purified by treatment with a weak basic resin before another precipitation from ethanol.

With gadolinium chloride: the mixture of 6.5 g of the octaacid and 3.5 g of $GdCl_3 \cdot 6H_2O$ in 130 ml of water is brought to pH 6.5 by addition of aqueous NaOH (1N) and is brought to 60° C. for 2 hours, during which the pH is maintained at 6.5 by addition of a total of 21 ml of 1N aqueous NaOH. After a few hours at ambient temperature, the mixture is concentrated to 25 ml and the final product is precipitated from 250 ml of $C_2H_5OH$ before being purified.

HPLC: 25 cm×4 mm Symmetry®–RP 18–5 μm column (Waters®)

UV detector at 200 nm mobile phase: 0.037N aqueous $H_2SO_4$ with $CH_3CN$ gradient (from 0% to 20% over 60 minutes); flow rate 1 ml/minute pair of isomers (a) (30%)* $t_r$=28–32 minutes pair of isomers (b) (65%)* $t_r$=32–36 minutes pair of isomers (c) (5%)* $t_r$=37–41 minutes

* percentage in the mixture, expressed with respect to the areas under the curve.

B. Isomerization of the Preceding Mixture:

A solution of 10 g of the preceding mixture in 100 ml of refluxing water is acidified by addition of HCl (1N) to pH 3. After stirring for 42 hours at this temperature, the solution is concentrated under reduced pressure to a volume of 10 ml and left to return to ambient temperature. 6 g of precipitated final product are isolated by filtration, which product comprises a trace of isomers (b). It can be purified by recrystallization from water.

If heating is carried out at only 80° C., 30% of the pair (b) still remains after heating for 150 hours and 10% still remains after 400 hours.

C. Amidation:

0.46 g of the pair of isomers obtained above and 2 g of N,N'-bis(2,3,4,5,6-pentahydroxyhexyl)-2,4,6-tribromo-5-(glycylamino)isophthalamide (compound IId of WO 97/1359) are dissolved in 8 ml of water, and a 6N aqueous NaOH solution is poured into the medium to pH 6 before introducing, at 40° C., 0.48 g of 1-(3-dimethylaminopropyl)-3-ethylcarbodiimide hydrochloride. The medium is maintained at 40° C. for 2 hours with stirring while introducing, from time to time, an N aqueous NCl solution in order for the pH not to exceed 7.

After returning to ambient temperature, the solution is poured into 100 ml of ethanol and the precipitate formed is isolated and then dissolved in 100 ml of water to produce a solution. This solution is subjected to tangential ultrafiltration through a polyether-sulphone membrane, the cutoff threshold of which is 1 Kdalton, in a Minisette® cell sold by Filtron®, USA.

After lyophilization, 1.5 g of the final product are isolated in the form of a white powder.

HPLC: 25 cm×4 mm Symmetry®–RP 18–5 μm column (Waters®)

UV detector at 230 nm mobile phase: 0.037N aqueous $H_2SO_4$ with $CH_3CN$, gradient from 99/1 to 90/10 (v/v) over 25 minutes, flow rate 1 ml/minute, $t_r$=6 to 20 minutes (several peaks).

EXAMPLE 2

Compound of Formula II in which

R = CH₂CONH 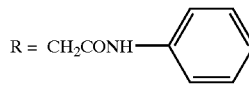 CONH 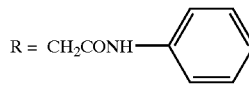 CONCH₂CONH 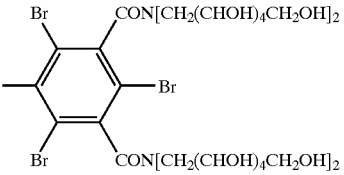
E

A. N,N'-bis(2,3,4,5,6-pentahydroxyhexyl)-2,4,6-tribromo-5-C4-[4-(aminoaetamido)benzamido]benzoylglycylamino)isophthalamide.

(a) 4-[4-Nitrobenzamido]benzoic acid:

100 g of 4-nitrobenzoyl chloride are introduced, little by little, into 74 g of 4-aminobenzoic acid and 360 ml of dimethylacetamide while maintaining the temperature at less then 25° C. After stirring for 24 hours, 500 ml of methylene chloride are added at 10° C. to precipitate the desired product. After washing with water and drying, 145 g of product are isolated.

(b) 4-[4-Aminobenzamido]bezoic acid;

A suspension of 136 g of the preceding acid in 1.8 liters of water, to which 240 ml of 1N aqueous NaOH solution and 14 g of palladium-on-charcoal (10%) have been added, is subjected to a hydrogen pressure of 0.6 MPa for 4 hours. The pH of the final suspension is then brought to approximately 10 before filtering through Celite® to remove the catalyst. The precipitate formed during the acidification of the filtrate to pH 5.3 is isolated and dried.

w=106 g; M.p. >260° C.

(c) 4-[4-(Phthalimidoacetamido)benzamido]benzoic acid:

32 ml of thionyl chloride are introduced dropwise into a solution of 90 g of phthalimidoacetic acid in 400 ml of dimethylacetamide at 10° C. and then, after stirring for 3 hours, 105 g of the amino acid obtained above are introduced at a temperature of less than 20° C. After stirring for 12 hours, the medium is poured into 4 liters of water and the isolated precipitate is washed with hot water.

Weight after drying: 176 g; M.p. >260° C.

(d) Chloride of the preceding acid:

2.5 ml of thionyl chloride are introduced into 10 g of the acid, in suspension in 50 ml of dioxare and 1 ml of dimethylformamide, and the mixture is kept stirred at 50° C. for 5 hours. After addition of one volume of diisopropyl ether, 10 g of precipitate are isolated.

The acid can also be suspended in toluene with tricaprylylmethylammonium chloride as catalyst.

(e) N,N'-Bis(2,3,4,5,6-pentahydroxyhexyl)-2,4,6-tribromo-5-(4-[4-(phthalimidoacetamido)benzamido]-benzoylglycylamino)isophthalamide:

A solution or 2.25 g of acid chloride with 5 g of N,N'-bis(2,3,4,5,6-pentahydroxyhexyl)-2,4,6-tribromo-5-(glycylalmino)isophthalamide and 0.7 ml of triethylamine in 25 ml of N-methylpyrrolidone is kept stirred for 12 hours; the $(C_2H_5)_2N \cdot HCl$ precipitate is then separated by filtration.

(f) Hydrazinolysis:

A solution of 1.4 equivalents of hydrazine hydrate in 6 ml of water is introduced into the preceding phthalimide solution at 70° C. After stirring for 2 hours at 90° C., the cooled mixture is poured into 125 ml of ethanol. 9 g of precipitate are isolated, from which the phthalylhydrazide is separated by precipitation or an aqueous solution at pH 2, before ultrafiltration at pH 6 through a polyamide membrane to remove the impurities of low mass. The final hydrochloride is subsequently isolated by lyophilization.

Yield; 50% from the acid chloride.

HPLC: 25 cm×4 mm Lichrospher® 100 Å–C18–5 μm column (Merck, Germany).

Eluent: $CH_3COOH$ in $H_2O$ (pH 3.3) and $CH_3CN$ (90/10 v/v);

flow rate 1 ml/min;

$t_r$=22, 24 and 27 minutes (3 peaks).

B. 0.28 g of the complex obtained in stage (B) of the preceding example and 2 g of the hydrochloride obtained in the preceding stage (A) are dissolved in 12.4 ml of water and the pH of the solution is brought to 6 by addition of N aqueous NaOH before adding 10 ml of a solution in dioxane of 0.2 g of 1-(3-dimethylaminopropyl)-3-ethylcarbodiimide hydrochloride and 0.024 g of hydroxybenzotriazole.

The solution is then stirred for 4 hours at ambient temperature while maintaining its pH at approximately 6, before being poured into 100 ml of ethanol. The precipitate formed is dissolved in 100 ml of water and the solution is ultrafiltered through a polyethersulphone membrane with a cutoff threshold of 30 Kdaltons.

After removing the solvent, 1.3 g of the desired product are obtained in the form of a white powder.

HPLC: 25 cm×6 mm Zorbax®–300 5B–C18–5 μm column (Hewlett-Packard)

UV detector: 290 nm

Eluent: aqueous $CH_3COONH_4$ (0.005M) with a $CH_3CN$ gradient (90/10 to 82/18) (v/v) over 60 minutes; flow rate 1 ml/min;

$t_r$=30 to 40 minutes (several peaks).

What is claimed is:

1. Process for the preparation of a racemic compound of formula III

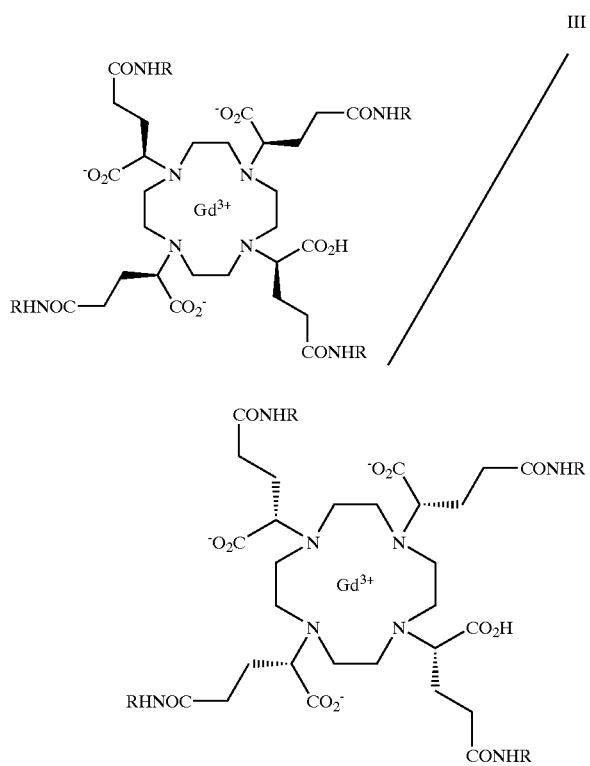

in which R is phenyl group or a linear, branched or cyclic ($C_1$–$C_8$) alkyl group which are substituted or interrupted by one or more groups selected from the group consisting of phenyl, alkyl, oxy, amino and amido groups, which may or may not be substituted by alkyl, it is being possible for the phenyl groups also to be substituted by one or more groups selected from the group selected from OH, Br, Cl, I, ($C_1$–$C_8$) alkyl, ($C_1$–$C_8$) alkyleneoxy $NO_2$, $NR_xR_y$, $NR_xCO_y$, CON-$R_xR_y$ and $COOR_x$, $R_x$ and $R_y$ being ($C_1$–$C_8$) alkyl or H, and it being possible for the linear or branched or cyclic alkyl groups to be hydroxylated, which consists:

in keeping an aqueous solution of the mixture of the stereoisomers of the gadolinium complex of 1,4,7,10-tetraazacyclododecane-1,4,7,10-tetra(2-glutaric acid), with a pH of between 2 and 4.5, at a temperature of greater than 70° C. for a few hours to a few days, so as to obtain the racemic mixture of octaacids of formula:

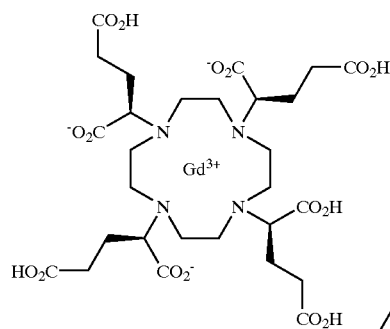

-continued

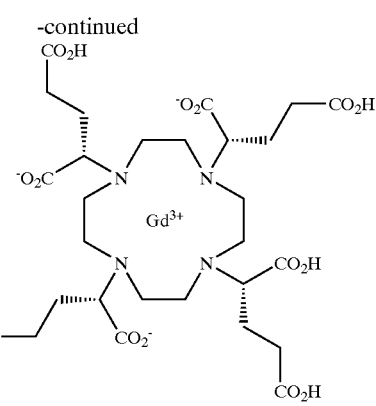

in reacting this mixture with the same amine $RNH_2$, with an agent which activates the acid functional group.

2. Process according to claim 1, in which the solution of complexed octaacid is maintained at its reflux temperature for 35 to 45 hours at pH 3.

* * * * *